(12) United States Patent
Allen, IV et al.

(10) Patent No.: US 10,772,673 B2
(45) Date of Patent: Sep. 15, 2020

(54) SURGICAL ENERGY SYSTEM WITH UNIVERSAL CONNECTION FEATURES

(71) Applicant: COVIDIEN LP, Mansfield, MA (US)

(72) Inventors: James D. Allen, IV, Broomfield, CO (US); Duane E. Kerr, Loveland, CO (US)

(73) Assignee: COVIDIEN LP, Mansfield, MA (US)

(*) Notice: Subject to any disclaimer, the term of this patent is extended or adjusted under 35 U.S.C. 154(b) by 720 days.

(21) Appl. No.: 15/143,703

(22) Filed: May 2, 2016

(65) Prior Publication Data

US 2017/0312004 A1    Nov. 2, 2017

(51) Int. Cl.
*A61B 18/14*    (2006.01)
*A61B 18/12*    (2006.01)
(Continued)

(52) U.S. Cl.
CPC ...... *A61B 18/1206* (2013.01); *A61B 18/1815* (2013.01); *A61B 34/35* (2016.02);
(Continued)

(58) Field of Classification Search
CPC ...... A61B 18/1206; A61B 2018/00178; A61B 2018/00994; A61B 2018/1273;
(Continued)

(56) References Cited

U.S. PATENT DOCUMENTS 5,766,167 A    6/1998 Eggers et al.
5,931,835 A    8/1999 Mackey
(Continued)

FOREIGN PATENT DOCUMENTS

DE    179607 C    3/1905
DE    390937 C    3/1924
(Continued)

OTHER PUBLICATIONS

Extended European Search Report issued in European Application No. 17168926.8 dated Oct. 9, 2017.
(Continued)

*Primary Examiner* — Jaymi E Della
*Assistant Examiner* — Sean W Collins
(74) *Attorney, Agent, or Firm* — Carter, DeLuca & Farrell, LLP (57) ABSTRACT

A surgical energy system includes a first and second surgical instruments and a generator including a universal interface. The first surgical instrument includes a first instrument connector having one or more instrument couplers disposed in a first instrument coupler configuration. The second surgical instrument includes a second instrument connector having one or more instrument couplers disposed in a second instrument coupler configuration. The first and second instrument coupler configurations are different. The generator includes a universal interface including generator couplers arranged to provide generator coupler configurations at the universal interface. Each generator coupler configuration accommodates one of the first and second instrument coupler configurations in order to electronically couple the generator to a respective one of the first and second surgical instruments.

20 Claims, 5 Drawing Sheets

(51) Int. Cl.
  *A61B 34/35*     (2016.01)
  *A61B 18/18*     (2006.01)
  *A61N 7/00*      (2006.01)
  A61B 90/90     (2016.01)
  A61B 18/20     (2006.01)
  A61B 17/00     (2006.01)
  A61B 18/00     (2006.01)

(52) U.S. Cl.
  CPC ............... *A61N 7/00* (2013.01); *A61B 18/14*
  (2013.01); *A61B 18/20* (2013.01); *A61B 90/90*
  (2016.02); *A61B 2017/00486* (2013.01); *A61B*
  *2018/00178* (2013.01); *A61B 2018/126*
  (2013.01); *A61B 2018/1253* (2013.01); *A61B*
  *2018/1273* (2013.01); *A61B 2018/1823*
  (2013.01)

(58) Field of Classification Search
  CPC ........ A61B 2018/1823; A61B 18/1815; A61B
    34/35; A61B 2017/00486; A61B 18/20;
    A61B 90/90; A61B 2018/126; A61B
    18/14; A61B 2018/1253; A61B 2562/22;
    A61B 2562/226; A61N 7/00; H01R
    35/04; H01R 39/643; H01R 41/00
  See application file for complete search history.

(56) References Cited

U.S. PATENT DOCUMENTS

| | | | |
|---|---|---|---|
| 5,997,528 A * | 12/1999 | Bisch ..................... | G06F 19/00 606/1 |
| 6,988,423 B2 | 1/2006 | Bolam et al. | |
| 7,156,844 B2 | 1/2007 | Reschke et al. | |
| 7,252,646 B2 | 8/2007 | Bolam et al. | |
| D574,323 S | 8/2008 | Waaler | |
| 8,182,480 B2 | 5/2012 | Huseman | |
| 8,613,627 B2 | 12/2013 | Selig et al. | |
| 8,968,311 B2 | 3/2015 | Allen, IV et al. | |
| 9,017,372 B2 | 4/2015 | Artale et al. | |
| 9,099,863 B2 | 8/2015 | Smith et al. | |
| 9,186,202 B2 | 11/2015 | Gilbert | |
| 9,270,202 B2 | 2/2016 | Johnson et al. | |
| 9,283,028 B2 | 3/2016 | Johnson | |
| 2004/0054364 A1 | 3/2004 | Aranyi et al. | |
| 2004/0097117 A1* | 5/2004 | Gonnering ......... | A61B 18/1206 439/218 |
| 2004/0097912 A1* | 5/2004 | Gonnering ......... | A61B 18/1206 606/34 |
| 2004/0167508 A1 | 8/2004 | Wham et al. | |
| 2005/0107831 A1* | 5/2005 | Hill ..................... | A61H 23/0245 607/2 |
| 2006/0079871 A1* | 4/2006 | Plaven ................... | A61B 18/14 606/34 |
| 2007/0032789 A1* | 2/2007 | Gonnering ............. | A61B 18/14 606/42 |
| 2009/0043293 A1* | 2/2009 | Pankratov ............ | A61B 18/203 606/9 |
| 2011/0224663 A1* | 9/2011 | Heim .................. | A61B 18/1206 606/33 |
| 2012/0202388 A1 | 8/2012 | Selig et al. | |
| 2013/0032491 A1 | 2/2013 | Nitta et al. | |
| 2014/0171935 A1 | 6/2014 | Digmann et al. | |
| 2014/0232463 A1 | 8/2014 | Gilbert | |
| 2014/0243815 A1 | 8/2014 | Kerr | |
| 2014/0253140 A1 | 9/2014 | Gilbert | |
| 2014/0257270 A1 | 9/2014 | Behnke | |
| 2014/0258800 A1 | 9/2014 | Gilbert | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |
| 2014/0358138 A1 | 12/2014 | Mattmiller et al. | |
| 2014/0376269 A1 | 12/2014 | Johnson et al. | |
| 2015/0025521 A1 | 1/2015 | Friedrichs et al. | |
| 2015/0025523 A1 | 1/2015 | Friedrichs et al. | |
| 2015/0032096 A1 | 1/2015 | Johnson | |
| 2015/0032098 A1 | 1/2015 | Larson et al. | |
| 2015/0032099 A1 | 1/2015 | Larson et al. | |
| 2015/0032100 A1 | 1/2015 | Coulson et al. | |
| 2015/0088116 A1 | 3/2015 | Wham | |
| 2015/0088117 A1 | 3/2015 | Gilbert et al. | |
| 2015/0088118 A1 | 3/2015 | Gilbert et al. | |
| 2015/0088124 A1 | 3/2015 | Wham | |
| 2015/0088125 A1 | 3/2015 | Wham | |
| 2015/0119871 A1 | 4/2015 | Johnson et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 4366724 A1 | 12/2003 |
| EP | 1776929 A1 | 4/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 1/1965 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |

OTHER PUBLICATIONS

Wald et al., "Accidental Burns", JAMA, Aug. 16, 1971, vol. 217, No. 7, pp. 916-921.

(56) References Cited

OTHER PUBLICATIONS

Vallfors et al., "Automatically Controlled Bipolar Electrosoagulation'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. Mi, Jan. Mar. 1964, pp. 16-27.
Cosman et al., "Methods of Making Nervous System Lesions", in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 11/242,458 dated Oct. 3, 2005 inventor: Becker.

\* cited by examiner

SURGICAL ENERGY SYSTEM WITH UNIVERSAL CONNECTION FEATURES

TECHNICAL FIELD

The present disclosure relates to surgical energy, and more particularly, the present disclosure is directed to apparatuses, systems and methods for coupling surgical instruments to surgical generators for effectuating energy-based tissue treatment.

BACKGROUND

Energy-based tissue treatment is well known in the art. Various types of energy (e.g., electrical, ultrasonic, microwave, cryogenic, heat, laser, etc.) are applied to tissue to achieve a desired result. For example, electrosurgery involves application of high radio frequency electrical current, microwave energy or resistive heating to a surgical site to cut, ablate, coagulate or seal tissue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

Still, given that energy-based treatment may involve many different apparatuses and/or systems, irrespective of the type of energy modality utilized; such treatment often requires multiple connectors, plugs, and/or the like for coupling and/or interchanging these apparatuses, systems, and/or components thereof in order to effectuate desired energy-based treatments.

SUMMARY

Accordingly, one aspect of the present disclosure is directed to a surgical energy system that includes first and second surgical instruments and a generator. The first surgical instrument includes a first instrument connector having one or more instrument couplers disposed in a first instrument coupler configuration. The second surgical instrument includes a second instrument connector having one or more instrument couplers disposed in a second instrument coupler configuration. The first and second instrument coupler configurations are different.

The generator includes a universal interface having generator couplers arranged to provide generator coupler configurations at the universal interface. Each generator coupler configuration is configured to accommodate one of the first and second instrument coupler configurations in order to electronically couple the generator to a respective one of the first and second surgical instruments.

In some embodiments, the generator includes one or more receptacles configured to receive one or more output modules. The one or more output modules may be configured to cooperate with one or more of the first and second surgical instruments when coupled to the generator. The one or more output modules may include an output energy module. The output energy module may include an inverter configured to output energy at an ultrasonic frequency, a microwave frequency, a radio frequency, or combinations thereof. In certain embodiments, the output module includes one or more mechanical components configured to transfer mechanical forces to the respective one of the first and second surgical instruments to enable the respective one of the first and second surgical instruments to perform one or more functions.

In certain embodiments, the one or more output modules may be configured to cooperate with one or more of the first and second surgical instruments when coupled to the generator. The one or more output modules may include a first output module and a second output module. One of the receptacles may removably receive a first one of the first and second output modules. The first one of the first and second output modules may be removable from one or more of the receptacles and replaceable with a second one of the first and second output modules.

In some embodiments, the receptacles may include a first receptacle and a second receptacle. One or more output modules may include a first output energy module and a second output energy module. The first output energy module may be configured to provide a first energy modality and the second output energy module may be configured to provide a second energy modality that is different from the first energy modality. The first receptacle may be configured to receive the first output energy module. The second receptacle may be configured to receive the second output energy module.

According to another aspect of the present disclosure, a generator includes a housing, a universal interface supported by the housing, and generator couplers coupled to the universal interface. The generator couplers are arranged to provide generator coupler configurations at the universal interface. A first one of the generator coupler configurations is configured to accommodate a first instrument connector and a second one of the generator coupler configurations is configured to accommodate a second instrument connector.

In some embodiments, the housing includes one or more receptacles configured to receive one or more output modules.

In certain embodiments, the housing includes receptacles configured to receive output modules. Each output module may be configured to cooperate with one or more of the first and second surgical instruments when coupled to the generator to enable the respective one of the first and second surgical instruments to perform one or more functions.

In some embodiments, one or more of the generator couplers are movable relative to the housing to facilitate coupling with one of the first and second instrument connectors of respective first and second instruments.

According to still another aspect of the present disclosure, a generator includes a housing, a universal interface supported by the housing, output modules, and receptacles supported within the housing. Each of the output modules is configured to cooperate with one or more surgical instruments when coupled to the universal interface. Each receptacle is configured to removably receive one or more of the output modules.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Particular embodiments of the present disclosure are described hereinbelow with reference to the accompanying drawings in which like reference numerals designate identical or corresponding elements in each of the several views. As used herein, the term "distal" refers to that portion of the system, apparatus and/or device, or component thereof, that are farther from the user, while the term "proximal" refers to that portion of the system, apparatus and/or device, or component thereof, that are closer to the user. In the following description, well-known functions or constructions are not described in detail to avoid obscuring the present disclosure in unnecessary detail.

Turning now to FIGS. 1-6B, a surgical energy system, in accordance with the present disclosure, generally referred to as 1, includes one or more surgical instruments 10, a generator 100, and one or more output modules 200. The one or more surgical instruments 10 and/or the one or more output modules 200 are selectively couplable to the generator 100. For a detailed description of the construction and operation of an example generator of which one or more components thereof can be included with generator 100, reference may be made to U.S. Patent Application Publication No. 20140171935, the entire contents of which are incorporated by reference herein.

Figure 1:
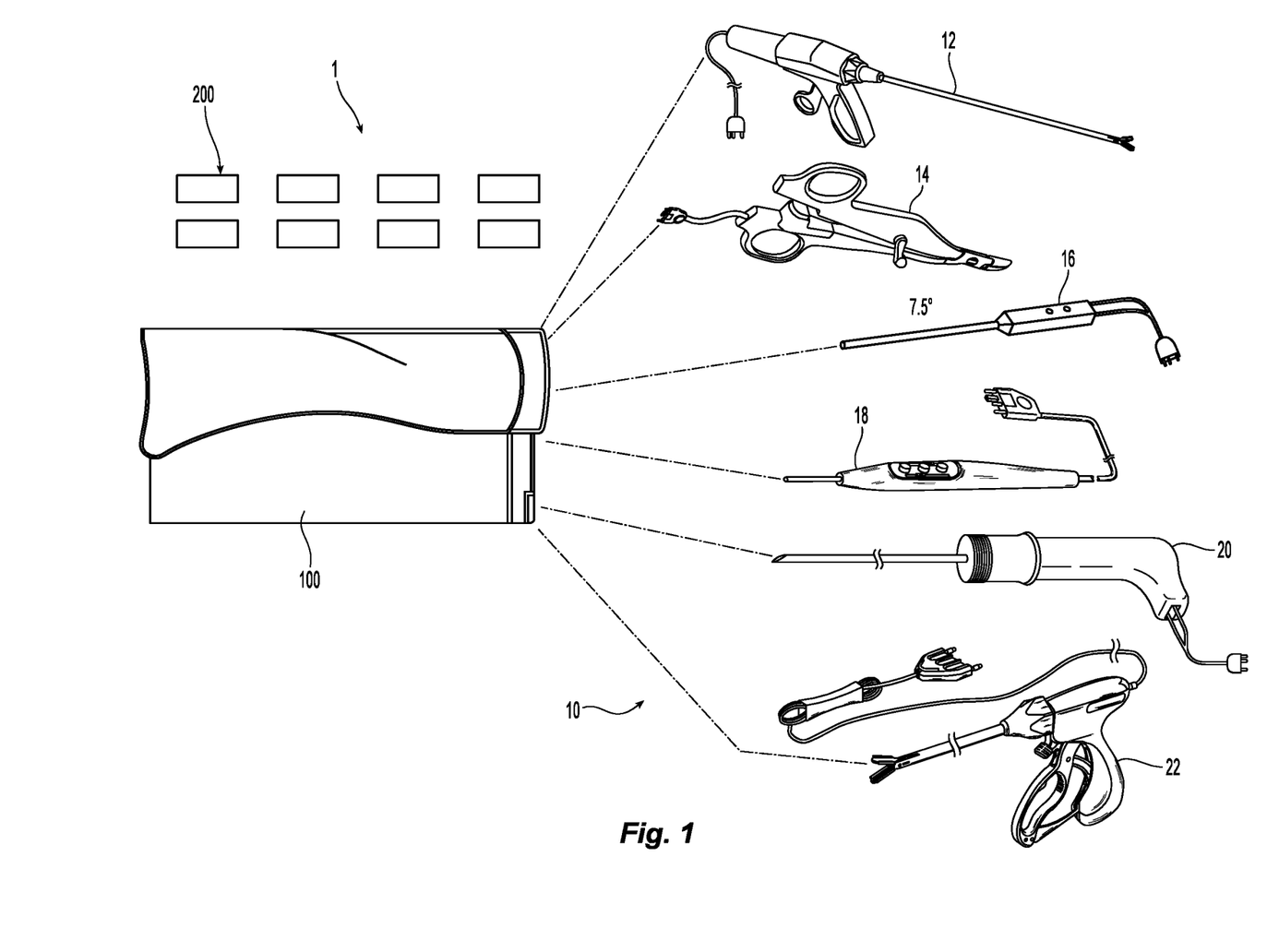
FIG. 1 is a schematic view of a surgical energy system according to the principles of the present disclosure.
Figure 2:
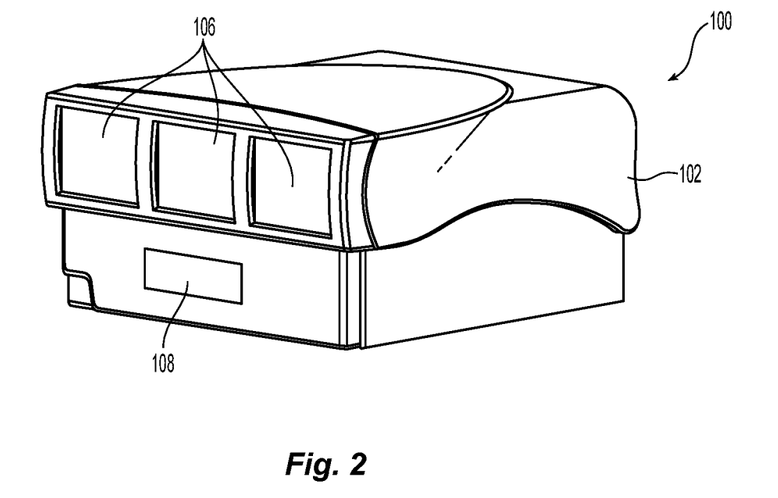
FIG. 2 is a front, perspective view of one embodiment of a generator of the surgical energy system of FIG. 1.
Figure 3:
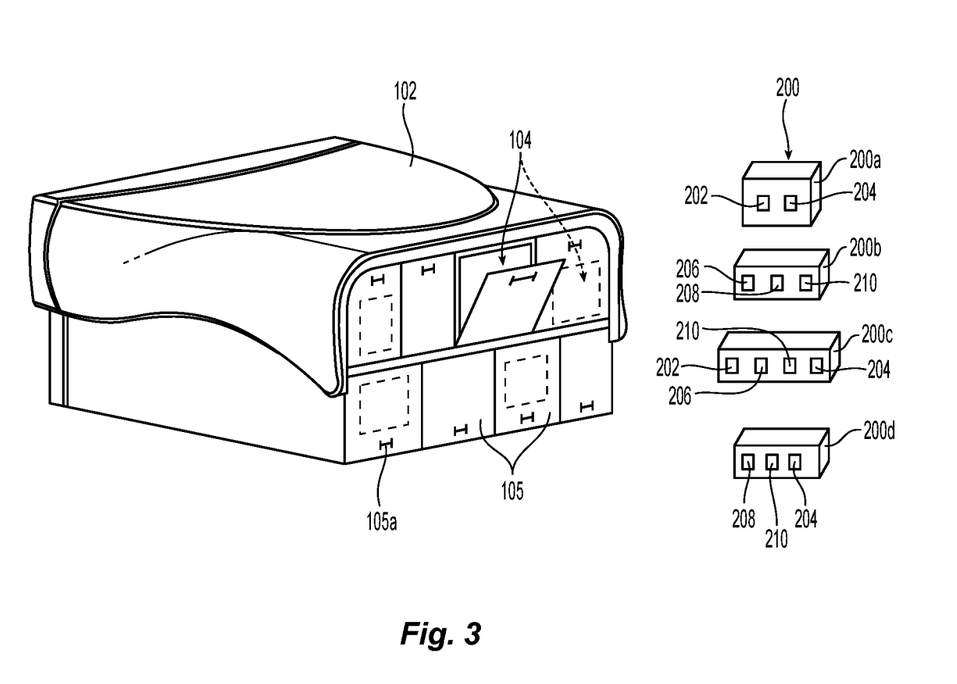
FIG. 3 is a rear, perspective view of the generator of FIG. 2.
Figure 4A:
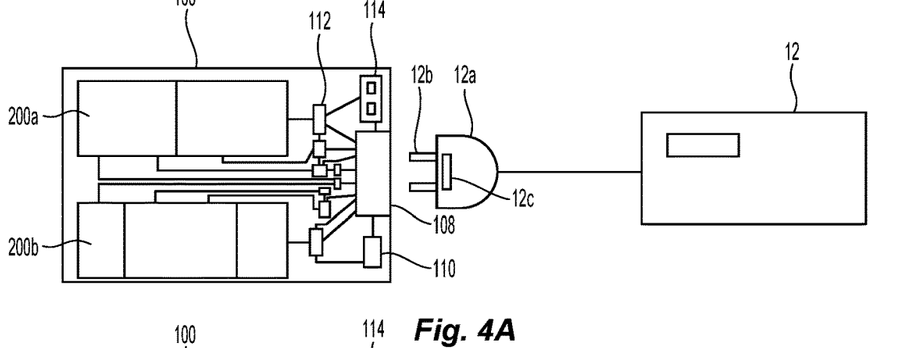
FIG. 4A-4D are schematic views illustrating various surgical instruments being coupled to the generator of FIG. 2.
Figures 4B, 4C, 4D:
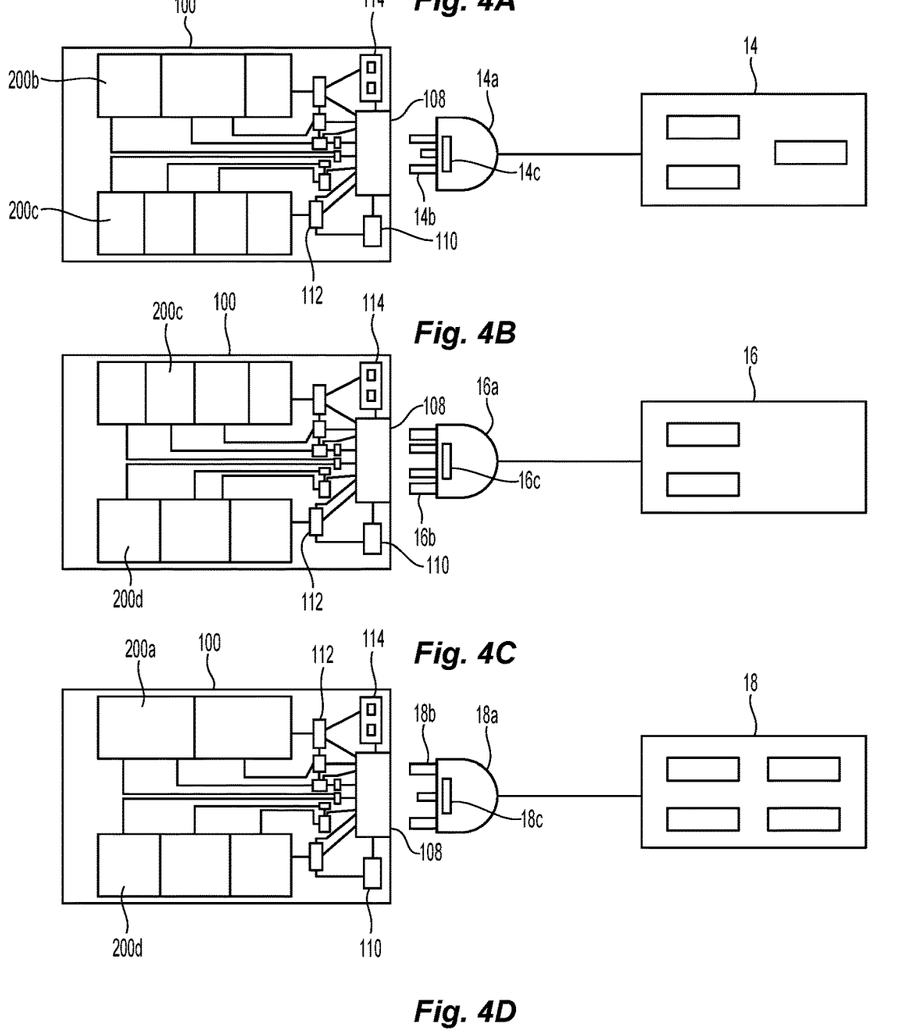

The one or more surgical instruments 10 may include any suitable surgical instrument such as an ultrasonic forceps 12, an open forceps 14, a suction coagulator 16, a surgical pencil 18, an ablation needle 20, a bipolar forceps 22, etc. The one or more surgical instruments 10 may be configured for any suitable energy-based tissue treatment such as electrical, ultrasonic, microwave, cryogenic, heat, laser, etc. For a detailed description of the construction and operation of example surgical instruments, reference may be made to U.S. Pat. No. 8,968,311 (bipolar forceps), U.S. Pat. No. 9,017,372 (open forceps), U.S. Pat. No. 7,156,844 (surgical pencil), U.S. Pat. No. 5,766,167 (monopolar forceps), U.S. Pat. No. 8,182,480 (suction coagulator), U.S. Patent Application Publication No. 2013/032491 (ablation needle), U.S. Patent Application Publication No. 2004/0054364 (ultrasonic), each of which is incorporated herein by reference.

As seen in FIGS. 4A-6B, each surgical instrument 10 includes an instrument connector such as instrument connectors 12a, 14a, 16a, 18a, 20a, and 22a of respective surgical instruments 12, 14, 16, 18, 20, and 22. Each instrument connector includes one or more instrument couplers such as instrument couplers 12b-22b such that each instrument connector includes one or more instrument couplers arranged in one of a plurality of different instrument coupler configurations. The one or more instrument couplers 12a-22a of the respective instruments 12-22 are arranged such that each of the respective instrument connectors 12a-22a includes a predetermined instrument coupler configuration corresponding to its respective instrument 12-22. For example, the instrument connector 12a of instrument 12 may include two instrument couplers 12b while the instrument connector 14a of instrument 14 may include three instrument couplers 14b. The instrument couplers 12b-22b can be provided in any suitable configuration such as any number, dimension, shape, and/or orientation. Depending on the type, style, modality, etc. of the respective surgical instrument 10, each instrument coupler configuration may be the same or different from the other instrument coupler configurations. In some embodiments, the predetermined instrument coupler configurations may be unique to a specific instrument of the one or more instruments 10.

In some embodiments, one or more of the instrument connectors 12a-22a may include one or more communication components (e.g. processors, sensors, etc.) such as communication components 12c-22c to provide communication and/or power between the respective surgical instrument 10 and the generator 100. One or more of the communication components 12c-22c may be configured to indicate the type of instrument to which the respective instrument connector 12a-22a is coupled (e.g., via stored information). In some embodiments, the communication components 12a-22a may include a bar code, Aztec code, and/or other readable indicia.

As seen in FIGS. 2, 3, and 4A-4D, the generator 100 includes a housing 102 that defines one or more receptacles 104 configured to receive the one or more output modules 200 (e.g., output modules 200a-200d). The one or more receptacles 104 may be in the form of a port having one or more electrical and/or mechanical couplings (not shown), and may include optical communication couplings, pneumatic couplings, and/or hydraulic couplings. The housing 102 includes one or more displays 106 and a universal interface 108 that are operatively coupled to a controller 110 (see FIGS. 4A-4D). The universal interface 108 is universal in that it is configured to couple to a plurality of instruments, one at a time. Advantageously, instead of having multiple interfaces and multiple connectors (e.g., plugs), each of which only mate with specific corresponding structure, a single interface provides a simplified generator with universal connection to accommodate various instruments. The universal interface 108 simplifies the instrument-to-generator connection by limiting the need for extraneous interfaces and the need to identify which connector and interface combination is appropriate for each instrument. In certain embodiments, the generator 100 includes multiple universal interfaces 108.

In some embodiments, the universal interface 108 may include mechanical and/or electrical components configured to provide a plug-and-play interface. The universal interface 108 may be electrically and/or mechanically coupled to one or more generator couplers 112 that couple to the one or more receptacles 104. In some embodiments, the universal interface 108 may be directly coupled to one or more of the receptacles 104 and/or one or more of the output modules 200.

In certain embodiments, the generator 100 may include one or more doors 105 that are moveable between open and closed positions to selectively provide access to the one or more receptacles 104. The doors 105 may include a handle 105a or like to enable a clinician to move the doors 105 between the open and closed positions.

With reference to FIGS. 4A-4D, the generator 100 may further include one or more instrument sensors 114 (e.g., scanner, diode, etc.) configured to sense the communication components 12c-22d of the surgical instruments 10 and communicate with the controller 110 and/or generator couplers 112. The controller 110 and/or generator couplers 112 may be configured to coordinate (e.g., via electronic circuitry, mechanical couplings, or the like) with the surgical instruments 10 and/or the output modules 100 to operate the surgical instruments 10 while the surgical instruments 10 are coupled to the generator 100. For example, the instrument sensor 114 may communicate an electrical signal to the controller 110 to indicate the type of instrument 10 coupled to the interface 108 based upon the communication component (e.g., communication component 12c). One or more of the generator couplers 112 can then communicate with one or more of the output modules 200 supported within the housing 102, whereby the one or more output modules 200 can cooperate with the instrument 10 (e.g., surgical instrument 12) operatively coupled thereto so that the instrument 10 can perform one or more functions (e.g., grasping, sealing, cutting, ablating, cooling, etc.).

The output modules 200 can include any suitable output module. In some embodiments, one or more of the output modules 200 may be an output energy module, a fluid/material supply and/or return module, a sensor module, etc. (e.g., output modules 200a-200d). For example, one or more of the output modules 200 can be configured to provide one or more various energy sources such as radiofrequency (e.g., bipolar, monopolar), laser/optic, pneumatics, hydraulics, microwave, chemical, plasma, light, etc.). The one or more output modules 200 may include any number of sensors (e.g., proximity, impedance, etc.). In some embodiments, one or more of the output modules 200 may be configured to supply and/or return fluids and/or materials, for instance, to tissue during a tissue sealing procedure. In some embodiments, the one or more output modules 200 include a gas supply module, a coolant supply module, or combinations thereof. One or more of the output modules 200 may be dependent and/or independent of one or more of the other output modules 200.

The output modules 200 may include one or more subcomponents 202, 204, etc. The one or more subcomponents 202, 204, 206, 208, 210, etc. may include any suitable mechanical, electrical, and/or chemical features such as inverters, microcontrollers, electrical wiring, gears, motors, cables, semi-conductors, pneumatics, hydraulics, cameras, scanners, etc. For instance, the one more output modules 200 may include an inverter configured to output energy at one or more of an ultrasonic frequency, a microwave frequency, a radio frequency, etc. In certain embodiments, different output modules may be configured to provide different energy modalities. In some embodiments, one of the output modules 200 may provide ultrasonic energy while another of the output modules 200 may provide radiofrequency energy such as monopolar or bipolar. In some embodiments, different output modules may be configured to provide the same energy modalities. In certain embodiments, one or more of the output modules 200 may provide multiple energy modalities.

In some embodiments, the one or more subcomponents 202, 204, 206, 208, 210 may include material or fluid sources such as collagen, plastic, biomaterials, argon, saline, etc. In certain embodiments, the one or more subcomponents 202, 204, 206, 208, 210 may provide a vacuum source.

In certain embodiments, the one more output modules 200 may include one or more subcomponents 202 that may include one or more mechanical components (couplers, bearings, shafts, cables, gears, motors, nuts, screws, pneumatics, hyradulics, etc.) configured to transfer mechanical forces to one or more surgical instruments 10 that couple to the generator 100 to enable the respective surgical instruments to perform a certain function.

In some embodiments, the generator 100 may include one or more output modules and/or other mechanical, electrical, and/or chemical components, etc. that may be integral with the generator 100.

In certain embodiments, the generator 100 and/or one or more of the output modules 200 may be configured to supply direct and/or alternating current, for example; to articulate, rotate, and/or fire a surgical instrument 10; power one or more motors; etc.

Figure 5A:
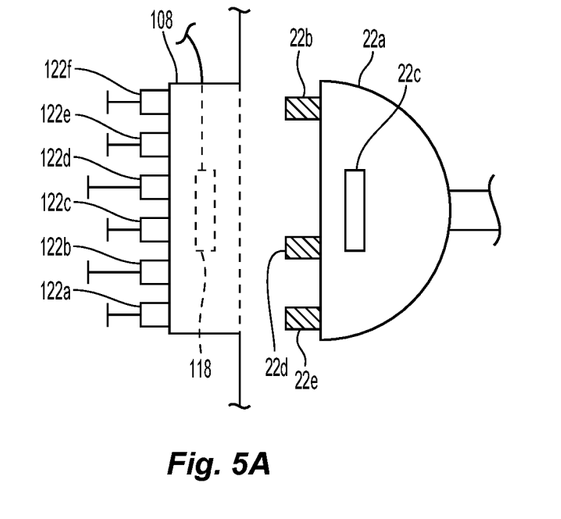
FIGS. 5A and 5B are progressive views illustrating a connector of a surgical instrument of the surgical energy system of FIG. 1 being coupled to the generator of FIG. 2.
Figure 5B:
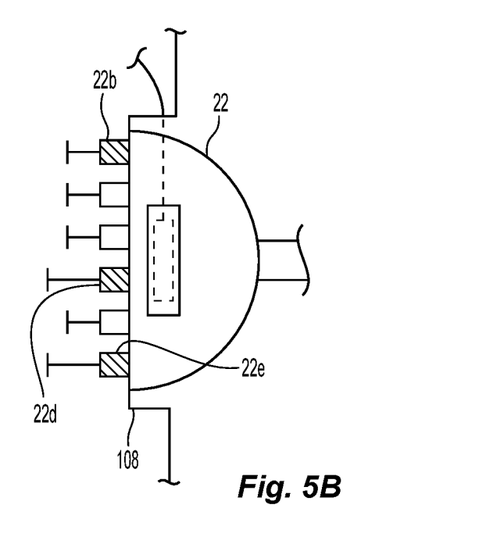

As seen in FIGS. 5A and 5B, the universal interface 108 includes generator couplers 122a-122f configured to receive instrument couplers such as instrument couplers 22b, 22e, and 22d of instrument connector 22a. The generator couplers 122a-122f are arranged to establish one or more predetermined generator coupler configurations in order to accommodate various surgical instruments 10, with each generator coupler configuration corresponding to one or more of the instrument coupler configurations of the surgical instruments 10 to individually accommodate or otherwise complement the instrument coupler configurations of one or more surgical instruments 10.

Figures 6A, 6B, 7:
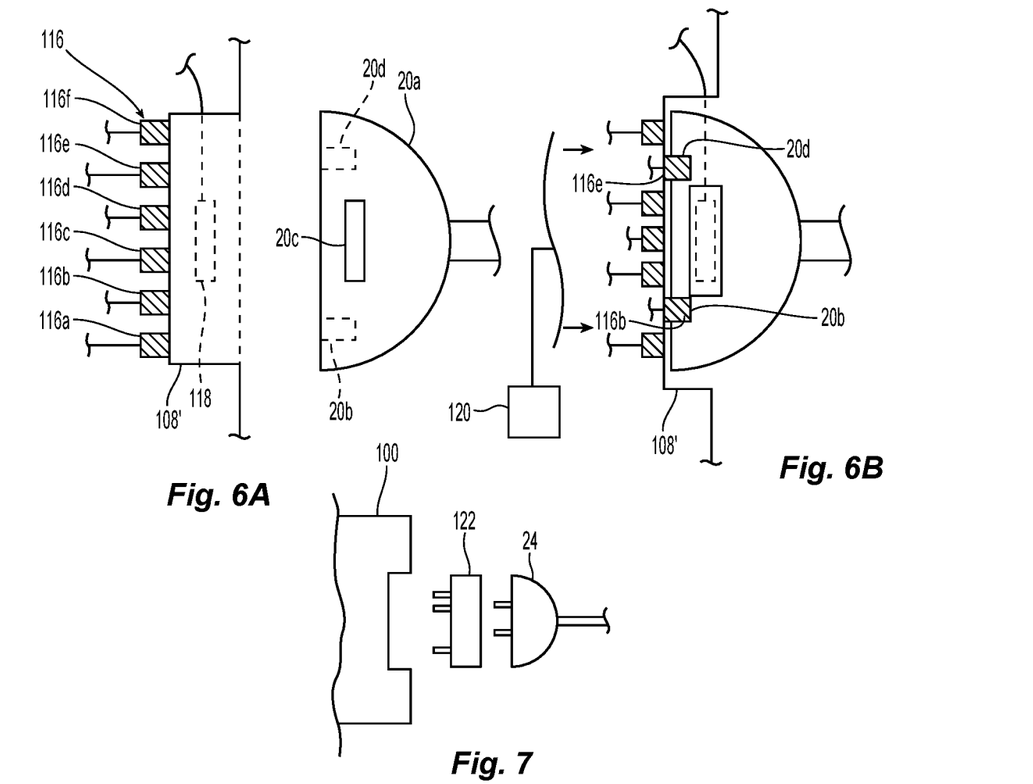
FIGS. 6A and 6B are progressive views illustrating a connector of another surgical instrument of the surgical energy system of FIG. 1 being coupled to another embodiment of the generator.
FIG. 7 illustrates one embodiment of an adapter in accordance with the principles of the present disclosure.

As seen in FIGS. 6A and 6B, one embodiment of the universal interface 108 includes a plurality of generator couplers 116 such as generator couplers 116a-116f that are configured to couple to the instrument couplers, such as instrument couplers 20b, 20d, of the respective instrument connectors, such as instrument connector 20a. The generator couplers 116a-116f may be movable relative to one or more of the other generator couplers 116a-116f to establish predetermined generator coupler configurations. For example, as seen in FIG. 6B, two of the generator couplers 116e, 116b may be moved toward corresponding instrument couplers 20b, 20d of instrument connector 20a to position the generator couplers 116e, 116d in a predetermined generator coupler configuration suitable to couple the instrument connector 20a to the universal interface 108. Of course, any number of the generator couplers can be arranged as desired to individually accommodate or otherwise complement any instrument connector. In some embodiments, the generator couplers 116a-116f and/or the instrument couplers, such as instrument couplers 20b, 20d, may be magnetically attracted to one another (e.g., via one or more magnetic and/or ferromagnetic materials).

In certain embodiments, movement of the generator couplers 116a-116f may be effectuated via a drive assembly 120 operatively coupled to the generator couplers 116a-116f in response to an identification of the type of instrument connector via a generator communication component 118 of the interface 108. The generator communication component 118 can be configured to sense or otherwise read the communication components 12c-22c of the instrument connectors 12a-22a to identify (to the controller 110) the type of instrument 10 to which the instrument connector 12a-22a is coupled so that the controller 110 can coordinate the operation of the components of the generator 100 and/or the surgical instrument 10 attached thereto. In response to a coupling (or an attempted coupling) of an instrument connector to the interface 108, the controller 110 may issue output such as connection or error notifications on the display 106 of the generator 100. The generator communication component 118 can be configured to detect any suitable information such size, style, types etc. of the surgical instrument 10 and/or components thereof (e.g., the respective instrument connector) so that the controller 110 can coordinate the appropriate energy, signals, etc.

As seen in FIG. 7, an adapter 24 can be coupled to an instrument connector 24, for example, to retrofit an older or outdated instrument connector or a different manufacturer's instrument connector to the universal interfaces of the present disclosure.

In some embodiments, the generator 100 may be configured to receive, store and/or send information such as patient medical records and/or one or more medical databases. The generator 100 may be configured to provide video and/or audio capture. In some embodiments, the generator 100 may be configured to create log files. In certain embodiments, the generator 100 may be configured to provide real-time and/or periodic data transfers. In some embodiments, the generator 100 may be configured to provide snapshot data (e.g., Ligasure™ seal data). In certain embodiments, the generator 100 may be configured to utilize information to predetermine modalities, connections, etc. as need for particular patients, procedures, etc. In some embodiments, the generator 100 may be configured to suggest configurations and/or default to a predetermined pre-op configuration.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors (including pneumatics and/or hydraulics), etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
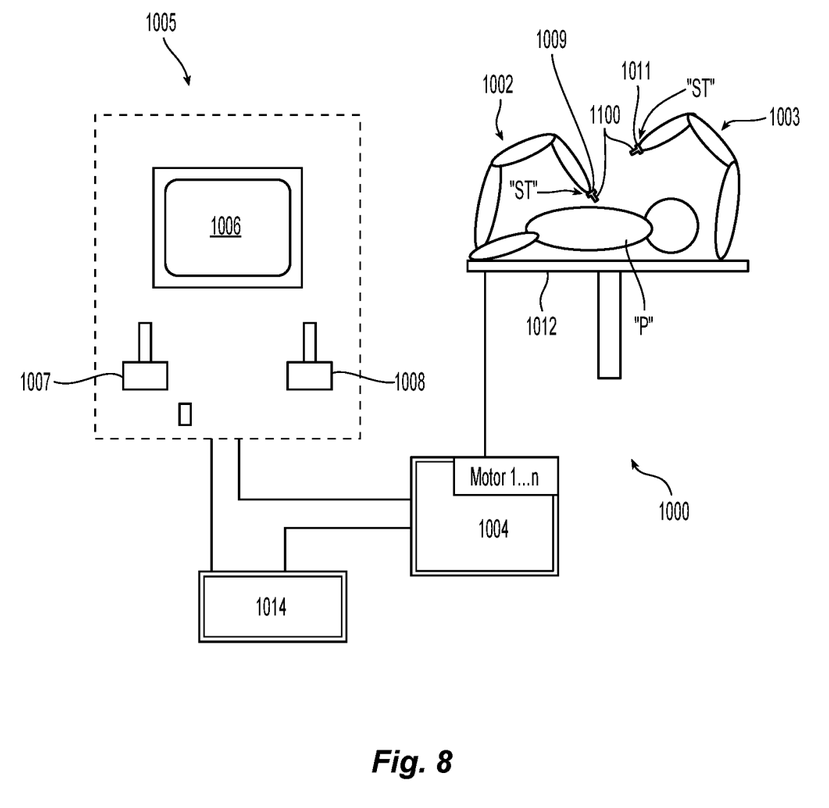
FIG. 8 is a schematic illustration of a medical work station and operating console in accordance with the present disclosure.

Referring also to FIG. 8, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members), in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A medical instrument or surgical tool (including an end effector 1100) may also be attached to the additional robot arm. The medical work station 1000 may include a database 1014 coupled with the control device 1004. In some embodiments, pre-operative data from patient/living being "P" and/or anatomical atlases may be stored in the database 1014.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A surgical energy system, comprising:
   a first surgical instrument including a first instrument connector having at least one first instrument coupler disposed in a first instrument coupler configuration;
   a second surgical instrument including a second instrument connector having at least one second instrument coupler disposed in a second instrument coupler configuration, the first and second instrument coupler configurations being different;
   a generator including a housing and a universal connector port, the universal connector port being a singular port and configured to receive one of the first instrument connector or the second instrument connector, the universal connector port including a plurality of generator couplers configurable into a first generator coupler configuration that interfaces with the at least one first instrument coupler disposed in the first instrument coupler configuration and a second generator coupler configuration that interfaces with the at least one second instrument coupler disposed in the second instrument coupler configuration in order to electrically couple the generator to a respective one of the first surgical instrument or the second surgical instrument;
   a generator communication component coupled to the generator and configured to identify the first and second surgical instruments and cause at least one of the plurality of generator couplers to move into the first generator coupler configuration or the second generator coupler configuration in response to the generator communication component identifying a respective one of the first or second surgical instruments; and
   at least one output module in electrical communication with the universal connector port, the at least one output module configured to transmit an energy to at least one of the first or second surgical instruments, the at least one output module configured to be removably secured in the housing of the generator.

2. The surgical energy system of claim 1, wherein the generator includes at least one receptacle configured to receive the at least one output module, the at least one output module configured to cooperate with at least one of the first or second surgical instruments when coupled to the generator.

3. The surgical energy system of claim 2, further comprising an output energy module coupled to the at least one output module and configured to transmit the energy to the at least one of the first or second instruments.

4. The surgical energy system of claim 3, wherein the output energy module includes an inverter configured to output the energy at an ultrasonic frequency, a microwave frequency, a radio frequency, or combinations thereof.

5. The surgical energy system of claim 3, wherein the output module includes at least one mechanical component configured to transfer mechanical forces to the respective one of the first or second surgical instruments to enable the respective one of the first and second surgical instruments to perform at least one function.

6. The surgical energy system of claim 1, wherein the at least one output module includes a plurality of output modules, and wherein the generator includes a plurality of receptacles, each of the plurality of receptacles configured to receive a respective output module of the plurality of output modules, each respective output module configured to cooperate with at least one of the first or second surgical instruments when coupled to the generator.

7. The surgical energy system of claim 6, wherein the plurality of output modules includes a first output module and a second output module, and wherein at least one of the plurality of receptacles removably receives a first one of the first or second output modules, the first one of the first or second output modules being removable from the at least one of the plurality receptacles and replaceable with a second one of the first or second output modules.

8. The surgical energy system of claim 6, wherein the plurality of receptacles includes a first receptacle and a second receptacle, wherein the plurality of output modules includes a first output energy module and a second output energy module, the first output energy module configured to provide a first energy modality and the second output energy module configured to provide a second energy modality that is different from the first energy modality, the first receptacle configured to receive the first output energy module, the second receptacle configured to receive the second output energy module.

9. The generator of claim 1, further comprising a drive assembly operatively coupled to the plurality of generator couplers for reconfiguring the plurality of generator couplers of the universal connector port.

10. A generator comprising:
    a housing;
    a universal connector port supported by the housing, the universal connector port being a singular port;
    a plurality of generator couplers coupled to the universal connector port and configurable into a first generator coupler configuration that interfaces with at least one first instrument coupler disposed in a first instrument coupler configuration and a second generator coupler configuration that interfaces with at least one second instrument coupler disposed in a second instrument coupler configuration;

a generator communication component configured to identify the at least one first instrument coupler and the at least one second instrument coupler and cause at least one of the plurality of generator couplers to move into the first generator coupler configuration or the second generator coupler configuration in response to the generator communication component identifying a respective one of the at least one first instrument coupler or the at least one second instrument coupler; and at least one output module in electrical communication with the universal connector port, the at least one output module configured to transmit an energy to at least one of the first or second instrument couplers, the at least one output module configured to be removably secured in the housing.

11. The generator of claim 10, wherein the housing includes at least one receptacle configured to receive the at least one output module, the at least one output module configured to cooperate with at least one of first or second surgical instruments when the at least one output module is coupled to at least one of the plurality of generator couplers.

12. The generator of claim 11, wherein the at least one output module includes at least one output energy module configured to output the energy at an ultrasonic frequency, a microwave frequency, a radio frequency, or combinations thereof.

13. The generator of claim 11, wherein the at least one output module includes at least one mechanical component configured to transfer mechanical forces to the at least one of the first or second surgical instruments to enable the at least one of the first or second surgical instruments to perform at least one function.

14. The generator of claim 10, wherein the at least one output module includes a plurality of output modules, and wherein the housing includes a plurality of receptacles configured to receive a respective output module of the plurality of output modules, each output module configured to cooperate with at least one of first or second surgical instruments when coupled to the generator to enable the at least one of the first or second surgical instruments to perform at least one function.

15. The generator of claim 10, wherein at least one of the plurality of generator couplers is movable relative to the housing.

16. The generator of claim 10, further comprising a drive assembly operatively coupled to the plurality of generator couplers for reconfiguring the plurality of generator couplers of the universal connector port.

17. A generator comprising:

a housing;

a universal connector port supported by the housing, the universal connector port being a singular port and including a plurality of generator couplers, the plurality of generator couplers configurable into a first generator coupler configuration that interfaces with at least one first instrument coupler disposed in a first instrument coupler configuration and a second generator coupler configuration that interfaces with at least one second instrument coupler disposed in a second instrument coupler configuration;

a generator communication component configured to identify the at least one first instrument coupler and the at least one second instrument coupler and cause at least one of the plurality of generator couplers to move into the first generator coupler configuration or the second generator coupler configuration in response to the generator communication component identifying a respective one of the at least one first instrument coupler or the at least one second instrument coupler;

a plurality of output modules, each of the plurality of output modules in electrical communication with the universal connector port, each of the plurality of output modules configured to transmit an energy to at least one of a plurality of surgical instruments when coupled to the universal connector port, each of the plurality of output modules configured to be removably secured in the housing; and a plurality of receptacles supported within the housing, each receptacle configured to removably receive at least one of the plurality of output modules.

18. The generator of claim 17, wherein at least one output module of the plurality of output modules includes an output energy module configured to output the energy at an ultrasonic frequency, a microwave frequency, a radio frequency, or combinations thereof.

19. The generator of claim 17, wherein at least one of the generator couplers is movable relative to the housing to facilitate coupling with at least one of the plurality of surgical instruments.

20. The generator of claim 17, wherein at least one output module of the plurality of output modules includes at least one mechanical component configured to transfer mechanical forces to at least one of the plurality of surgical instruments to enable the at least one of the plurality of surgical instruments to perform at least one function.

* * * * *